United States Patent
Schuetz et al.

(10) Patent No.: US 7,368,243 B2
(45) Date of Patent: May 6, 2008

(54) DETECTION OF NUCLEIC ACIDS TO ASSESS RISK FOR BOVINE SPONGIFORM ENCEPHALOPATHY

(75) Inventors: Ekkehard Schuetz, Gottingen (DE); Leonid Iakoubov, San Ramon, CA (US); Howard Urnovitz, Iowa City, IA (US)

(73) Assignee: Chronix Biomedical, San Jose, CA (US)

( * ) Notice: Subject to any disclaimer, the term of this patent is extended or adjusted under 35 U.S.C. 154(b) by 2 days.

(21) Appl. No.: 11/178,246

(22) Filed: Jul. 8, 2005

(65) Prior Publication Data
US 2006/0068419 A1 Mar. 30, 2006

Related U.S. Application Data

(60) Provisional application No. 60/586,556, filed on Jul. 9, 2004.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search ............ None
See application file for complete search history.

(56) References Cited

U.S. PATENT DOCUMENTS 6,033,858 A * 3/2000 Bastian .................. 435/6

FOREIGN PATENT DOCUMENTS

| WO | WO 97/34015 A1 | 9/1997 |
|----|----|----|
| WO | WO 01/42504 A2 | 6/2001 |
| WO | WO 02/079511 A1 | 10/2002 |

OTHER PUBLICATIONS

Van Keulen, L.M.J. et al., Veterinary Quarterly, vol. 22, pp. 197-200 (2000).*
Brenig, Bertram et al., "Zelluläre Nucleinsäuren im Serum und Plasma als neue diagnostische Werkzeuge" *Berl. Münch. Tierärztl. Wschr.* 115:122-124 (2002).
Durie, Brian G. M. et al., "RT-PCR Amplicons in the Plasma of Multiple Myeloma Patients," *Acta Oncologica* 39(7): 789-796 (2000).
Gibson, Toby J., "RuNAway Disease: A two cycle model for transmissible spongiform encephalopathies (TSEs) wherein SINE proliferation drives PrP overproduction," *Genome Biology* 2(7): preprint0006.1-6.17 (2001).
Tsiu, Nancy B. Y. et al., "Stability of Endogenous and Added RNA in Blood Specimens, Serum, and Plasma," *Clinical Chemistry* 48(10): 1647-1653 (2002).
Urnovitz, Howard B., "RNAs in the Sera of Persian Gulf War Veterans Have Segments Homologous to Chromosome 22q11.2," *Clinical and Diagnostic Laboratory Immunology* 6(3): 330-335 (May 1999).

* cited by examiner

*Primary Examiner*—Teresa Strzelecka
(74) *Attorney, Agent, or Firm*—Townsend and Townsend and Crew LLP

(57) ABSTRACT

The present invention provides a method of detecting abnormal serum nucleic acid profiles to assess the risk of a transmissible spongiform encephalopathy, e.g., BSE.

10 Claims, 8 Drawing Sheets

Sequences derived from PCR CHX1F/CHX1R

SEQUENCE LISTING

<160> NUMBER OF SEQ ID NOS: 13

<210> SEQ ID NO 1
<211> LENGTH: 18
<212> TYPE: DNA
<213> ORGANISM: Artificial
<220> FEATURE:
<223> OTHER INFORMATION: PCR Primer CHX-1F

<400> SEQUENCE: 1
agctgaccga cgaggagg                                          18

<210> SEQ ID NO 2
<211> LENGTH: 22
<212> TYPE: DNA
<213> ORGANISM: Artificial
<220> FEATURE:
<223> OTHER INFORMATION: PCR primer CHX-1R

<400> SEQUENCE: 2
agtttcttgc ctggagaatc cc                                     22

<210> SEQ ID NO 3
<211> LENGTH: 18

```
<212> TYPE: DNA
<213> ORGANISM: Artificial
<220> FEATURE:
<223> OTHER INFORMATION: consensus short interspersed nuclear element
      (SINE) PCR Primer #55F

<400> SEQUENCE: 3
cttgcctgga gaatccca                                                     18

<210> SEQ ID NO 4
<211> LENGTH: 18
<212> TYPE: DNA
<213> ORGANISM: Artificial
<220> FEATURE:
<223> OTHER INFORMATION: consensus short interspersed nuclear element
      (SINE) PCR Primer #55R

<400> SEQUENCE: 4
gggattctcc aggcaaga                                                     18

<210> SEQ ID NO 5
<211> LENGTH: 17
<212> TYPE: DNA
<213> ORGANISM: Artificial
<220> FEATURE:
<223> OTHER INFORMATION: PCR Primer #60F

<400> SEQUENCE: 5
gcatgttcct ttcagaa                                                      17

<210> SEQ ID NO 6
<211> LENGTH: 18
<212> TYPE: DNA
<213> ORGANISM: Artificial
<220> FEATURE:
<223> OTHER INFORMATION: PCR Primer #60R

<400> SEQUENCE: 6
gttgcttcag tcgtgtcc                                                     18

<210> SEQ ID NO 7
<211> LENGTH: 19
<212> TYPE: DNA
<213> ORGANISM: Artificial
<220> FEATURE:
<223> OTHER INFORMATION: PCR Primer #61R

<400> SEQUENCE: 7
ctgtgtccta ggaatgcat                                                    19

<210> SEQ ID NO 8
<211> LENGTH: 20
<212> TYPE: DNA
<213> ORGANISM: Artificial
<220> FEATURE:
<223> OTHER INFORMATION: PCR Primer #62F

<400> SEQUENCE: 8
gcatcaaagc actgtacgtt                                                   20

<210> SEQ ID NO 9
<211> LENGTH: 21
<212> TYPE: DNA
<213> ORGANISM: Artificial
<220> FEATURE:
<223> OTHER INFORMATION: PCR Primer #62R
```

-continued

```
<400> SEQUENCE: 9
gccttctaga gtcaaccaag a                                               21

<210> SEQ ID NO 10
<211> LENGTH: 21
<212> TYPE: DNA
<213> ORGANISM: Artificial
<220> FEATURE:
<223> OTHER INFORMATION: PCR Primer #63F

<400> SEQUENCE: 10
cgtgcaatgc aggagaccag g                                               21

<210> SEQ ID NO 11
<211> LENGTH: 20
<212> TYPE: DNA
<213> ORGANISM: Artificial
<220> FEATURE:
<223> OTHER INFORMATION: PCR Primer #63R

<400> SEQUENCE: 11
gctgtgacat ttcttgatag                                                 20

<210> SEQ ID NO 12
<211> LENGTH: 15
<212> TYPE: DNA
<213> ORGANISM: Artificial
<220> FEATURE:
<223> OTHER INFORMATION: PCR control Primer #PGO1-5

<400> SEQUENCE: 12
aagcacttct gtttc                                                      15

<210> SEQ ID NO 13
<211> LENGTH: 18
<212> TYPE: DNA
<213> ORGANISM: Artificial
<220> FEATURE:
<223> OTHER INFORMATION: PCR control Primer #PGO2-5

<400> SEQUENCE: 13
cattcagggg ccggagga                                                   18
```

DETECTION OF NUCLEIC ACIDS TO ASSESS RISK FOR BOVINE SPONGIFORM ENCEPHALOPATHY

CROSS-REFERENCE TO RELATED APPLICATIONS

This application claims benefit of U.S. provisional application No. 60/586,556, filed Jul. 9, 2004, which application is incorporated by reference herein.

BACKGROUND OF THE INVENTION

Mad cow disease or bovine spongiform encephalopathy (BSE) is a progressive, invariably fatal neurodegenerative disease in cattle. BSE was recognized as a public health concern in 1996 when young Britons were diagnosed with what appeared to be a new form of a familial illness of older age, Creutzfeldt-Jakob Disease (CJD). British scientists linked the development of this "variant Creutzfeldt-Jakob Disease" (vCJD) to exposure to and/or consumption of BSE cattle. As of November 2002, 143 cases of "definite or probable" vCJD had been diagnosed in the UK.

The European Union has created a policy to cull cohorts in herds of cattle in which a BSE marker is detected. Cohorts, which have an approximately 100-fold increased BSE risk, are defined as all animals born and/or raised in the same herd as a confirmed BSE or prion-positive case within twelve months before and after the date of birth of the BSE index case. Cohort culling is most often accomplished through back-tracing from a slaughterhouse detection. Unfortunately, new variant cases of BSE in cattle younger than twenty four months in Japan and France appear to indicate a change in the clinical parameters of BSE (Biacabe, et al. in *Int. Conf. of Prion Diseases: From basic Research to intervention concepts.* 44Munich; 2003; Casalone, et al. in *Int. Conf. of Prion Diseases: From basic Research to intervention concepts.* 256Munich; 2003).

Early stage spongiform encephalopathies are difficult to detect by prion testing because prion accumulation is most often associated with late-stage disease. Genetic tests for prion gene polymorphisms are currently used to determine the susceptibility of sheep for scrapie (Hunter, et al. *Arch Virol* 141:809-824, 1996). No such diversity of prion genes is found in BSE. However, the detection of nucleic acids in cattle sera (Brenig, Schutz, & Urnovitz, *Berl Munch Tierarztl Wochenschr* 115:122-124, 2002) has previously been reported. Tests for detection and monitoring of genetic material associated with chronic illnesses other than BSE can be performed using sera. Such serum nucleic acids (SNA) associated tests are often designed to detect unique nucleic acid targets, usually of exogenous origin, e.g. HIV-1, CMV, HCV and HBV. SNAs of possible endogenous origin also have been found to be associated with chronic illnesses in humans (Urnovitz, et al. *Clin Diagn Lab Immunol* 6:330-335, 1999; Durie, Urnovitz, & Murphy *Acta Oncol* 39:789-796, 2000). However, this approach has not been applied to detection of transmissible spongiform encephlopathies.

It has been suggested that current tests are not sensitive enough to fully protect against the entry of BSE cattle into the human food chain (Knight, *Nature* 426:216, 2003). Further, current tests cannot identify cohort herd mates of BSE-infected cattle that have an increased risk of BSE. The current invention addresses this need.

BRIEF SUMMARY OF THE INVENTION

This invention is based on the discovery that abnormal nucleic acid profiles are detected in acellular fluid samples, e.g., serum or plasma, from animals at risk for transmissible spongiform encephalopathy, e.g., BSE. The invention therefore provides a method of detecting an animal at increased risk for bovine spongiform encephalopathy (BSE), the method comprising: incubating nucleic acids extracted from an acellular sample obtained from the animal with amplification primers in a test amplification reaction; detecting reactivity of the amplification reaction that is over 3 standard deviations from a reference amplification reaction, wherein reactivity of over 3 is indicative of an increased risk for BSE. In some embodiments, the acellular fluid sample is serum or plasma. The nucleic acid sample can be a DNA sample or RNA sample.

Any number of primers can be used in the methods of the invention. Typically, at least one primer hybridizes to sequences in a noncoding region of the genome; often one of the primers comprises sequences that hybridize to repetitive sequences, e.g., SINE sequence, in the animal genome. In some embodiments, the primers need not be from contiguous sequences or sequence on the same chromosome. In exemplary embodiments, the primers hybridize to the same sequences as the primer CHX-1F and CHX-1R. Such primers can, for example, comprise at least 10 contiguous nucleotide of CHX-1F and CHX-1R. In some embodiments, the hybridizing region of a primer comprises at least 80%, typically 90% identity to SEQ ID NO:1 or SEQ ID NO:2.

In typical embodiments, the amplification characteristic that is analyzed in the methods of the invention is a melting curve. The melting profile can be determined at the end of an amplification reaction or at a particular cycle number. In other embodiments, the amplification characteristic that is analyzed is a pattern on a gel, e.g., a polyacrylamide gel.

Often, the amplification reactions comprise a compound that specifically binds to double-stranded DNA, e.g., a fluorescent dye.

The invention also provides a kit comprising primers that hybridize to sequences that are indicative of an increased risk for BSE, e.g., primers that hybridize to the same sequences as the primers CHX-1F and CHX-1R. In some embodiments, the kit comprises the primers CHX-1F and CHX-1R. Such a kit can also comprise various controls and reagents, including, e.g., a reference sample.

In another aspect, the invention provides a method of identifying primers to use in an amplification reaction to detect at animal at increased risk for bovine spongiform encephalopathy (BSE), the method comprising: identifying nucleic acid sequences that are enriched in BSE animals compared to normal; designing primers based on the sequences that are enriched in BSE relative to normal animals; and selecting primers that detect reactivity in an amplification reaction comprising nucleic acids from a cohort or BSE animal that is over 3 standard deviations from a reference amplification reaction. Typically, the enriched sequences are identified in acellular samples, such as serum. The nucleic acids in the amplification reaction that identifies primers are often isolated from acellular samples, e.g., serum.

The invention also provides a method of detecting an animal at increased risk for bovine spongiform encephalopathy (BSE), the method comprising: incubating nucleic acids extracted from an acellular sample obtained from the animal with amplification primers obtained in accordance with the method described herein, e.g., the preceding paragraph, in a test amplification reaction; and detecting reactivity of the amplification reaction that is over 3 standard deviations from a reference amplification reaction, wherein reactivity of over 3 is indicative of an increased risk for BSE.

DETAILED DESCRIPTION OF THE INVENTION

Definitions

Figure 1A:
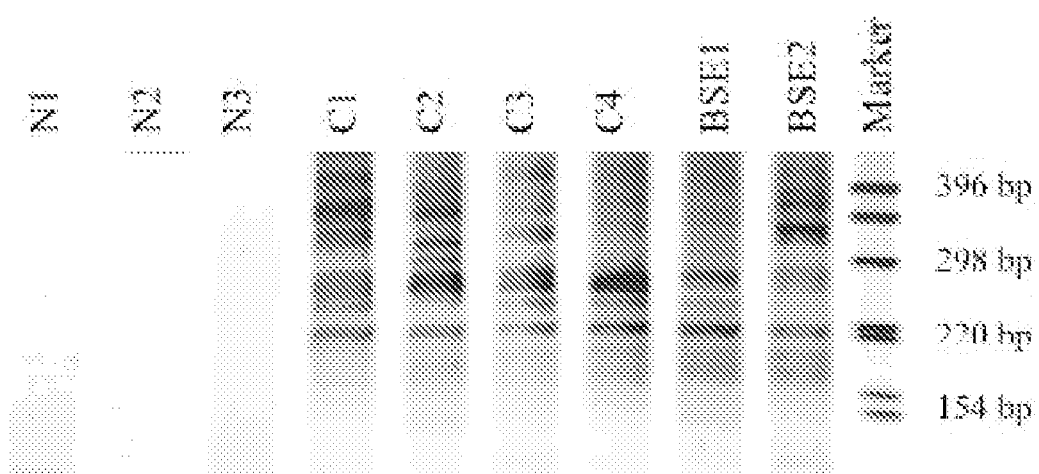
FIG. 1A provides exemplary data showing post-PCR (CHX-1F/CHX-1R) PAGE analysis from sera of two BSE cattle, four BSE-exposed cohort animals, and three normal controls. Lanes 1 to 3: Normal control samples N1 to N3; lanes 4 to 7: Cohort samples C1 to C4; lane 8 and 9: PrPres positive BSE cases BSE1 and BSE2; lane 10: Bp markers with size shown at the right.
Figure 1B:
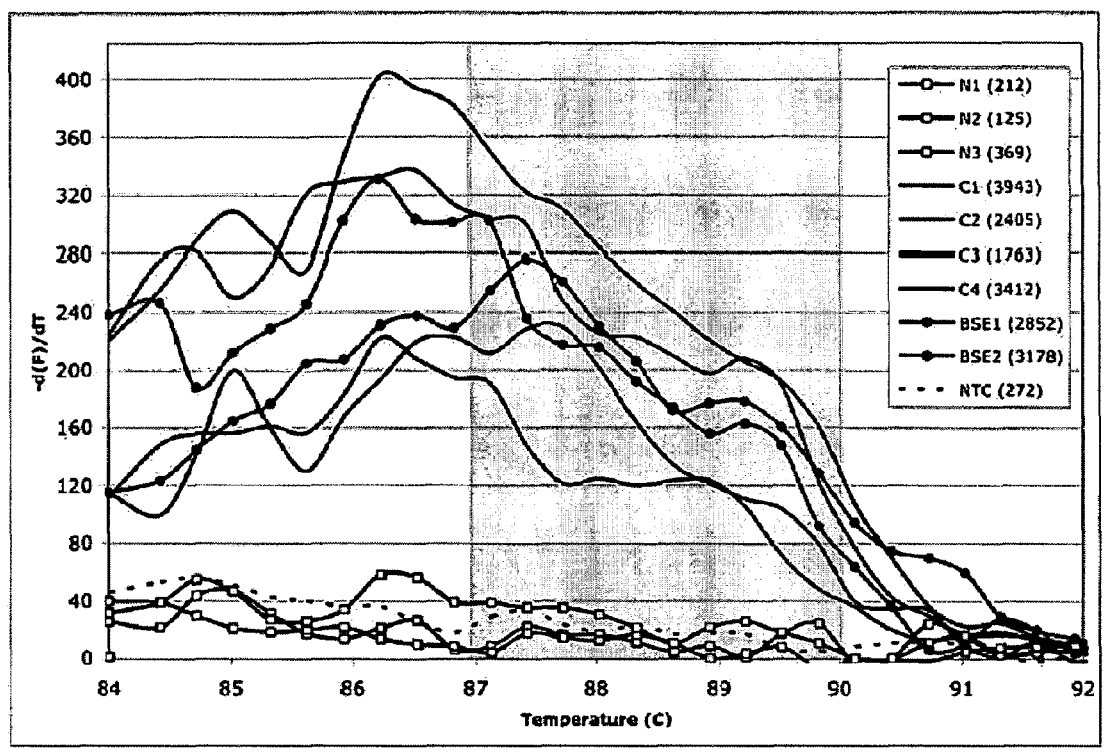
FIG. 1B provides exemplary data that shows melting curves from the same experiment as shown in FIG. 1A. 30 cycles of PCR with primers CHX-1F and CHX-1R were performed. The difference of cohort (C1 to C4, solid lines) and BSE samples (BSE1 and BSE2, closed circles) within the diagnostic range (87 to 90° C.) are statistically significant (p<0.01) vs. NTC (non-template control, dotted line) and vs. normals (N1 to N3, open circles).
Figure 2:
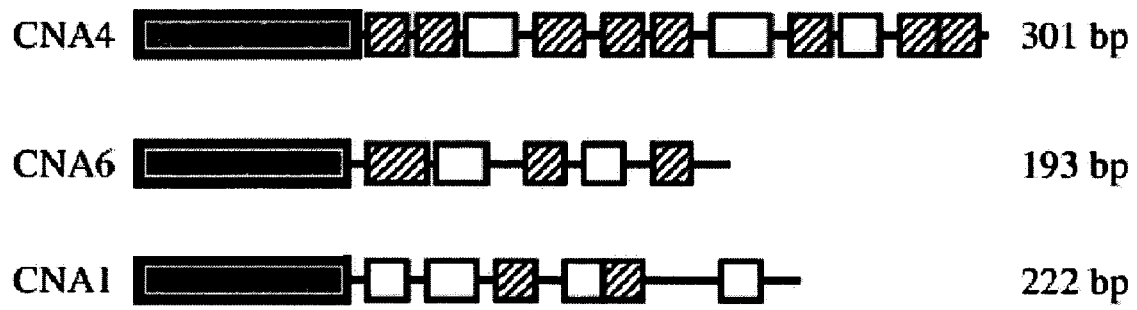
FIG. 2 shows DNA sequence alignments (5' to 3', left to right) from three individual CNA fragments derived from PCR with CHX-1F/CHX-1R primers. A common element identified from two confirmed BSE cases, depicted as a solid gray box, in all CNA fragments is homologous to the monomer region of the Bov-tA SINE sequence (Acc. No. X64124). The 5' Bov-tA-like sequence is followed 3' downstream with homologous fragments derived from Acc. No. AC092496. CNA6 is a sequence identified from BSE cow 1 and cohort sera. The 5' Bov-tA-like sequence is followed 3' downstream with homologous fragments derived from Acc. No. AC091728.2. CNA1 is a sequence identified from BSE cow 2 and cohort sera. The 5' Bov-tA-like sequence is followed 3' downstream with homologous fragments derived from Acc. No. AC091660.2. Open boxes are plus/plus homologies (11 to 20 bp); diagonally-striped boxes are plus/minus homologies (11 to 20 bp).
Figure 3:
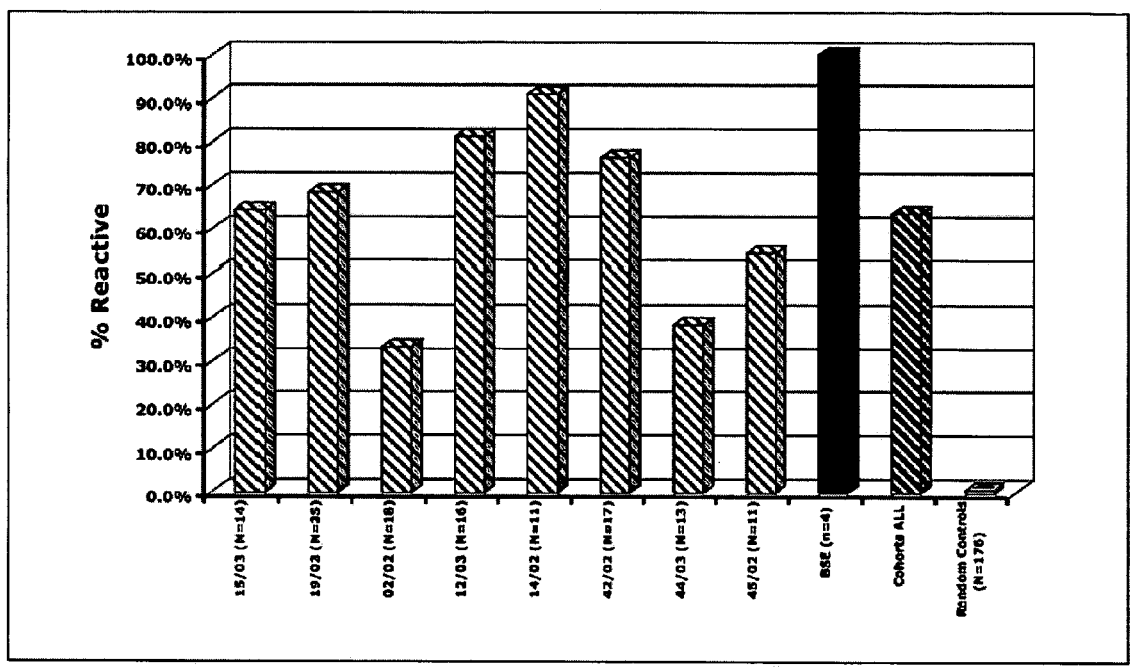
FIG. 3 provides exemplary data showing percent reactivity of four confirmed BSE cases (solid black bar), eight unrelated BSE cohorts and healthy control animals. All eight cohorts (diagonally striped bars—cohort numbers are given according to Table 3) showed a higher proportion of repeatedly reactive samples than random healthy controls (solid gray bar), ranging from 33% to 91% of each cohort. Only one healthy control out of 176 was found to be repeatedly reactive (0.6%). The differences between cohorts and an apparently healthy control herd as well as randomly selected cattle without detectable PrPres post mortem are highly significant (p<0.001).

A "cohort" refers to birth or feeding cohorts that are defined according to the official EU definition as being raised or born on the same farm within 12 months prior to or after a BSE index case.

An "increased risk for BSE" refers to a greater risk of developing BSE than that of a healthy animal that has not been exposed to another animal that has BSE, e.g., a cohort animal. For example, there is over a 100-fold increased risk of cohort cows being $Prp^{res}$ positive compared to cows that are not cohort animals.

The term "reactivity" as used herein refers to a change in a characteristic of an amplification characteristics, e.g., a melting curve, in the presence of a nucleic acid sequence that is indicative of an increased risk for a disease, e.g, BSE. A sample is considered reactive when it exhibits a value of at least 3, preferably 5 standard deviations above a reference standard.

A "positive reference" or "positive control" is a sample that is known to contain nucleic acids that are indicative of risk of a disease, e.g., BSE. In some embodiments, a "positive reference" can be from a known cohort animal that was reactive in the assay of the invention. Alternatively, a "positive reference" can be a synthetic construct that shows reactivity in an assay of the invention.

A "reference control" is a sample that results in minimal change to the amplification characteristic analyzed for the presence of nucleic acids associated with increased risk for BSE. Often, such a sample is a known negative, e.g., from healthy animals. For example, in diagnostic applications, such a control is typically derived from a normal animal that is not a cohort with a $PrP^{res}$ animal. A "reference control" is preferably included in an assay, but may be omitted.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid.

An "amplification characteristic" refers to any parameter of an amplification reaction. Such reactions typically comprises repeated cycles. An amplification characteristic may be the number of cycles, a melting curve, temperature profile, or band characteristics on a gel or other means of post-amplification detection.

A "melting profile" or "melting curve" refers to the melting temperature characteristics of a nucleic acid fragment over a temperature gradient. In some embodiments, the melting curve is derived from the first derivative of the melting signal. The melting point of a DNA fragment depends, e.g., on its length, its G/C content, the ionic strength of the buffer and the presence of mismatches (heteroduplexes). Thus, the proportion of the molecules in the population that are melting over a temperature range generates a melting profile, which is unique to a particular fragment or population of molecules.

The term "amplification reaction" refers to any in vitro means for multiplying the copies of a target sequence of nucleic acid. Such methods include but are not limited to polymerase chain reaction (PCR), DNA ligase, (LCR), QβRNA replicase, RNA transcription-based (TAS and 3SR) amplification reactions, and nucleic acid sequence based amplification (NASBA). (See, e.g., *Current Protocols in Human Genetics* Dracopoli et al. eds., 2000, John Wiley & Sons, Inc.).

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; *PCR Technology: Principles and Applications for DNA Amplification* (Erlich, ed., 1992) and *PCR Protocols: A Guide to Methods and Applications*, Innis et al., eds, 1990.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-25 nucleotides, in length. The length and sequences of primers for use in PCR can be designed based on principles known to those of skill in the art, see, e.g., Innis et al., supra. A primer is preferably a single-stranded oligodeoxyribonucleotide. The primer includes a "hybridizing region" exactly or substantially complementary to the target sequence, preferably about 15 to about 35 nucleotides in length. A primer oligonucleotide can either consist entirely of the hybridizing region or can contain additional features which allow for the detection, immobilization, or manipulation of the amplified product, but which do not alter the ability of the primer to serve as a starting reagent for DNA synthesis. For example, a nucleic acid sequence tail can be included at the 5' end of the primer that hybridizes to a capture oligonucleotide. As appreciated by one of skill in the art, a primer for use in the invention need not exactly correspond to the sequence(s) that it amplifies in a hybridization reaction. For example, the incorporation of mismatches into a probe can be used to adjust duplex stability when the assay format precludes adjusting the hybridization conditions. The effect of a particular introduced mismatch on duplex stability is well known, and the duplex stability can be routinely both estimated and empirically determined, as described above. Suitable hybridization conditions, which depend on the exact size and sequence of the probe, can be selected empirically using the guidance provided herein and well known in the art (see, e.g., the general PCR and molecular biology technique references cited herein).

The term "subsequence" when referring to a nucleic acid refers to a sequence of nucleotides that are contiguous within a second sequence but does not include all of the nucleotides of the second sequence.

A "temperature profile" refers to the temperature and lengths of time of the denaturation, annealing and/or extension steps of a PCR reaction. A temperature profile for a PCR reaction typically consists of 10 to 60 repetitions of similar or identical shorter temperature profiles; each of these shorter profiles may typically define a two step or three-step PCR reaction. Selection of a "temperature profile" is based on various considerations known to those of skill in the art, see, e.g., Innis et al., supra.

A "template " refers to a double or single stranded polynucleotide sequence that comprises a polynucleotide to be amplified.

An "acellular biological fluid" is a biological fluid that substantially lacks cells. Typically, such fluids are fluids prepared by removal of cells from a biological fluid that normally contains cells (e.g., whole blood). Exemplary processed acellular biological fluids include processed blood (serum and plasma), e.g., from peripheral blood or blood from body cavities or organs; and samples prepared from urine, milk, saliva, sweat, tears, phlegm, cerebrospinal fluid, semen, feces, and the like. Often, serum or plasma is the acellular sample that is analyzed in the assays of the invention. Other acellular samples that can be used include samples comprising nucleic acids obtained by washing any cell preparation to remove circulating nucleic acids that are associated with the cell surface. For example, such an acellular sample can be obtained by washing circulating blood cells, such as lymphocytes. The supernatant from the wash can then be analyzed.

"Nucleic acid" refers to a deoxyribonucleotide or ribonucleotide polymer in either single- or double-stranded form, or chimeric constructs of polynucleotides chemically linked to reporter molecules, and unless otherwise limited, would encompass known analogs of natural nucleotides that can function in a similar manner as naturally occurring nucleotides.

The term "biological sample", as used herein, refers to a sample obtained from an organism or from components (e.g., cells) of an organism. The sample may be of any biological tissue or fluid. Frequently the sample will be a "clinical sample" which is a sample derived from a patient, animal or human, with a disease or suspected of having a disease. Such samples include, but are not limited to, sputum, blood, serum, plasma, body cavity blood or blood products, blood cells (e.g., white cells), tissue or fine needle biopsy samples, urine, milk, peritoneal fluid, and pleural fluid, or cells therefrom. Biological samples may also include sections of tissues such as frozen sections taken for histological purposes.

An "individual" or "patient" as used herein, refers to any animals, often mammals, including, but not limited to humans, nonhuman primates such as chimpanzees and monkeys, horses, cows, deer, sheep, goats, pigs, dogs, minks, elk, cats, lagromorphs, and rodents.

A "chronic illness" is a disease, symptom, or syndrome that last for months to years. Examples of chronic illnesses in animals include, but are not limited to, cancers and wasting diseases as well as autoimmune diseases, and neurodegenerative diseases such as spongiform encephalopathies and others.

"Repetitive sequences" refer to highly repeated DNA elements present in the animal genome. These sequences are usually categorized in sequence families and are broadly classified as tandemly repeated DNA or interspersed repetitive DNA (see, e.g., Jelinek and Schmid, *Ann. Rev. Biochem.* 51:831-844, 1982; Hardman, *Biochem J.* 234:1-11, 1986; and Vogt, *Hum. Genet.* 84:301-306, 1990). Tandemly repeated DNA includes satellite, minisatellite, and microsatellite DNA. Interspersed repetitive DNA includes Alu sequences, short interspersed nuclear elements (SINES) and long interspersed nuclear elements (LINES).

A "rearranged sequence" or "recombined sequence" is a region of the genomic DNA that is rearranged compared to normal, i.e., the rearranged sequence is not contiguous in genomic DNA in healthy animals or in genomic DNA obtained from animals prior to contracting a disease or prior to exposure to a genotoxic agent.

A "fragile site" is a locus within an animal genome that is a frequent site of DNA strand breakage. Fragile sites are typically identified cytogenetically as gaps or discontinuities as a result of poor staining. Fragile sites are classified as common or rare and further divided according to the agents used to induce them. For a general description of fragile sites and their classification, see, Shiraishi et al., *Proc. Natl. Acad. Sci USA* 98:5722-7 (2001), Sutherland *GATA* 8:1961-166 (1991). Exemplified sequences disclosed herein include sequences that are found in rearrangements of host genomic DNA or viral genomes that have apparently been inserted into the animal genome at a fragile site. Thus, fragile sites can contain "archived nucleic acid sequences" that are from the host and/or pathogens, including bacteria, parasites, and viruses.

The term "substantially identical" indicates that two or more nucleotide sequences share a majority of their sequence. Generally, this will be at least about 80%, 85%, or 90% of their sequence and preferably about 95% of their sequence. The percent identity can be determined using well know sequence algorithms or by manual inspection. Another indication that sequences are substantially identical is if they hybridize to the same nucleotide sequence under stringent conditions (see, e.g., Sambrook and Russell, eds, *Molecular Cloning: A Laboratory Manual,* 3rd Ed, vols. 1-3, Cold Spring Harbor Laboratory Press, 2001; and *Current Protocols in Molecular Biology,* Ausubel, ed. John Wiley & Sons, Inc. New York, 1997). Stringent conditions are sequence-dependent and will be different in different circumstances. Generally, stringent conditions are selected to be about 5° C. (or less) lower than the thermal melting point (Tm) for the specific sequence at a defined ionic strength and pH. The $T_m$ of a DNA duplex is defined as the temperature at which 50% of the nucleotides are paired and corresponds to the midpoint of the spectroscopic hyperchromic absorbance shift during DNA melting. The $T_m$ indicates the transition from double helical to random coil or the reverse.

Typically, stringent conditions will be those in which the salt concentration is about 0.2×SSC at pH 7 and the temperature is at least about 60° C. For example, a nucleic acid of the invention or fragment thereof can be identified in standard filter hybridizations using the nucleic acids disclosed here under stringent conditions, which for purposes of this disclosure, include at least one wash (usually 2) in 0.2×SSC at a temperature of at least about 60° C., usually about 65° C., sometimes 70° C. for 20 minutes, or equivalent conditions. For PCR, an annealing temperature of about 5° C. below Tm, is typical for low stringency amplification, although annealing temperatures may vary between about 32° C. and 72° C., e.g., 40° C., 42° C., 45° C., 52° C., 55° C., 57° C., or 62° C., depending on primer length and nucleotide composition. High stringency PCR amplification, a temperature at, or slightly (up to 5° C.) above, primer Tm is typical, although high stringency annealing temperatures can range from about 50° C. to about 72° C., and are often 72° C., depending on the primer and buffer conditions (Ahsen et al., *Clin Chem.* 47:1956-61, 2001). Typical cycle conditions for both high and low stringency amplifications include a denaturation phase of 90° C.-95° C. for 30 sec-2 min., an annealing phase lasting 30 sec.-10 min., and an extension phase of about 72° C. for 1-15 min.

Introduction

Bovine spongiform encephalopathy (BSE) is clinically characterized by increasing perturbation of central nervous function in the affected animal, ultimately leading to severe symptoms, e.g., an inability to stand, forcing the sacrifice of the animal. In contrast to other mammalian transmissible spongiform encephalopathies, the bovine form does not appear to be associated with a mutation in the prion gene, but is caused by a post-translational misfolding of the prion protein, which leads to aggregation in the central nervous system. The diagnosis is based on the fact that misfolded prion protein has enhanced resistance to protease K digestion. As disease-specific prion accumulation in the plasma or blood of animals has not been identified, the diagnostic target has been the brain stem. Therefore, there is an urgent need to define a blood-borne marker for TSEs so that the disease can be diagnosed in living animals, in particular in animals that may be at increased risk for the disease, e.g., cohort animals, such as cows in the same herd as an infected animal.

The invention provides a method for diagnosing an increased risk for BSE using primers in an amplification reaction, which amplification reaction detects animals at-risk for BSE.

Nucleic Acids Detected in the Methods of the Invention

Nucleic acid molecules detected in the methods of the invention may be free, single or double stranded, molecules or complexed with protein. The detected nucleic acids can be DNA or RNA molecules. RNA molecules need not be transcribed from a gene, but can be transcribed from any sequence in the chromosomal DNA. Exemplary RNAs include miRNA, intergenic RNA, small nuclear RNA (snRNA), mRNA, tRNA, rRNA, and interference RNA (iRNA).

The nucleic acid molecules may comprise sequences transcribed from repetitive sequences or intergenic DNA in the genome of the individual from which the sample is derived. The detected nucleic acid molecules may also be the products of rearrangement of germline sequences and/or sequences introduced into the genome, e.g., exogenous viral sequences.

The method does not require knowledge of the polynucleotide sequences present in the test samples to be evaluated. Thus, a polynucleotide detected using this method may be a particular polynucleotide or may be a population of polynucleotides that are present in the sample. Furthermore, even in instances, where the polynucleotide to be detected has a known sequence, the polynucleotide in a particular sample, need not have that sequence, i.e., the sequence of the polynucleotide in the sample may be altered in comparison to the known sequence. Such alterations can include mutations, e.g., insertions, deletions, substitutions, and various other rearrangements. Further, the resulting amplified products may be as result of the amplification reaction and not reflect the original pool of polynucleotides.

Test Samples

The test samples are typically biological samples that comprise target nucleic acids. A target nucleic acid can be from any source, but is typically from a biological sample that comprises small quantities of nucleic acid, e.g., nucleic acid samples obtained from acellular fluids that are not readily quantified by standard PCR methodology. In particular embodiments, the test sample is a nucleic acid, e.g., RNA or DNA that is isolated from serum or plasma.

Amplification Reactions

Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Amplification reactions to amplify the nucleic acids in the samples are performed using standard methodology. The test sample to be evaluated is included early, typically at the onset, of the amplification reaction. Typically, the amplification reaction is a PCR.

The primers to be used in the PCR typically include at least one primer that is from a non-coding region. Preferably, the primer amplifies a sequence that comprises repetitive elements, e.g., Alu-like or SINE sequences, or sequences involved in rearrangements. In some embodiments, the individual primers in a primer pair need not hybridize to sequences that are present on a same unrearranged chromosome. The ability of such primers to amplify nucleic acids that are indicative of risk for BSE can be determined empirically.

Primers can also be selected by enriching for disease-associated amplicons present in acellular fluids, e.g., serum, in BSE and/or cohort animals, but not normal animals. This can be performed using known techniques, such as differential display. Preferably, sequences that are enriched in BSE acellular samples are present in at least one BSE animal, but not normal animals. For example, identification of sequences enriched or unique to BSE, can be accomplished by using degenerate primers in the amplification of BSE and healthy sera. The resulting amplicons can be analyzed, for example, using gel analysis. Bands in the gel analysis that are unique to BSE samples, i.e., bands that are observed in all BSE-confirmed samples, but not in healthy control samples, can be isolated and sequenced. These sequences are then used to select unique candidate primers, e.g., using standard methodology as described in Example 1. The primers are evaluated for their ability to show significant separation of samples from BSE-confirmed animals over samples from healthy controls, e.g., using PCR or PAGE gels.

In one embodiment, the primers are CHX-1F, 5'-AGCTGACCGACGAGGAGG-3' (SEQ ID NO:1) and CHX-1R, 5'-AGTTTCTTGCCTGGAGAATCCC-3' (SEQ ID NO:2). As understood by one of skill in the art, CHX-1F and CHX-1R sequences can be modified such that they still amplify the sequences of interest. For example, at least 3 nucleotides can be changed in the sequences. In some embodiments, a primer for use in a method of the invention to detect an increased risk for BSE comprise at least 10 contiguous nucleotides of SEQ ID NO:1 or SEQ ID NO:2. In other embodiments, such a primer is at least 80% identical, often 90% or 95% identical to SEQ ID NO:1 or SEQ ID NO:2.

The amplification reaction can be monitored either during amplification or at the end of amplification. The reaction is monitored using various known techniques. In one embodiment, the amplification reaction mixture comprises doubled-stranded specific nucleic acid dyes. These dyes, typically fluorescent, specifically intercalate into double-stranded nucleic acids relative to single-stranded nucleic acid molecules. Accordingly, they can be used to monitor the amount of double-stranded nucleic acid present during various stages of the amplification reaction or at the end of the amplification reaction. Such dyes include SYBR®Green I and Pico Green.

Various characteristics of the test nucleic acid amplification reaction can be changed by the presence of the nucleic acids associated with an increased risk for BSE. These include cycle number changes and melting curve parameters. These endpoints can be measured during the amplification reaction or at the end of the amplification reaction. For example, in using cycle number as an endpoint parameter, the amount of product generated/cycle can be assessed during the reaction. The presence of nucleic acids associated with an increased risk for BSE is detected by an alteration in the amount of product generated through the course of the reaction, or alternatively, at a particular cycle number.

Other methods for measuring differences in the products of an amplification reaction include known techniques such as single strand conformation polymorphism (SSCP) mass-spectrometry, e.g., MALDI-TOF, ESI-QTOF, APCI-TQMS or APCI-MSn, capillary electrophoresis, such as that performed for microsatellite analysis, or denaturing HPLC, combined with either UV, fluorescence, or using an ESI or APCI interface with any mass spectrometry detection, which can also be done with capillary electrophoresis separation.

In some embodiments, melting curve analysis is used as an endpoint for analysis of the test nucleic acid samples.

Determination of Test Sample Melting Curve Parameters

The conditions for defining whether a sample is considered to be reactive, i.e., the sample contains nucleic acid sequences associated with BSE, vs. whether it is considered to be unreactive is established by running negative and positive controls samples. The maximum signal separation between negative and positive references are determined, i.e., temperatures are identified that can be used for area under the curve ratios that give maximum separation between the negative and positive controls. Typically, the area under the curve analysis is performed at a range of 87° C. to 90° C. This range is used as it is not prone to the influence of non-specific products, e.g., primer-dimers, which frequently may be present. Reactivity of each individual sample is calculated on the basis of an area under the curve above the detection limit, which is defined as mean +3, typically mean +5, standard deviations above baseline of non-template or reference controls.

Various controls are often included in the reaction. These include a non-template control, samples from known healthy animals, and a known positive control. A non-template control is a reaction in which no sample is added to the PCR. The reference controls are samples known to be normal, e.g., from cows known to be negative for an increased risk for BSE. The positive control may be an artificial positive control or can be from a source that is known to be at increase risk for BSE, e.g., a cohort animal. An assay need not contain all of the controls. Further, some control values, e.g., a reference control, can be supplied from previously performed assays.

As explained above, the presence of the nucleic acid associated with BSE risk is determined by a significantly different alteration in the test sample, as compared to the references standards.

Analysis of Melting Curve for Test Samples The test samples are normally run concurrently with the positive and references controls. This monitoring will provide a melting profile of the amplified product. Typically, the Tm is obtained in a separate melting process at the end of the amplification cycle, during which fluorescence is continuously monitored and a melting profile is obtained. However, a Tm may also be obtained at some point during the amplification process.

Fluorescence monitoring is generally used to produce the melting curves. For example, double-stranded-specific DNA specific dyes, e.g., SYBR® Green, can be incorporated into the amplification reaction or added to the reaction only for detection purposes after the amplification. SYBR® Green dye is thought to bind within the minor groove of dsDNA; thus the fluorescent signal steadily decreases as the dsDNA melts into single strands. Thus, a specific probe is not required to monitor the reaction. Typical melting curve analyses are described in the following examples.

Analogous methodology can be employed to determine the endpoint standards for any amplification parameter to be tested. For example, the cycle number in the presence of positive and negative reference standards is determined and the mean and standard deviations calculated to select a cutoff value for whether a sample is considered to be reactive or unreactive. Further, analyses such as electrophoresis can be used to assess the presence of reaction products.

EXAMPLES

Example 1

Detection of Animals at an Increased Risk for BSE

This example describes detection of an increased risk for BSE. In summary, a PCR using non-coding region primers in a differential display approach was used on the sera from four confirmed cases of BSE, 135 BSE-exposed cohort animals associated with 8 confirmed BSE cases and 176 healthy, PrPres-negative control cows. All 4 sera from BSE confirmed cases were reactive in the assay. BSE-exposed cohorts had a range of 33% to 91% reactive individuals per cohort, compared to only <1% among healthy controls (p<0.001). Cloning of the reactive PCR products revealed bovine germ-line rearranged sequences. All sequenced PCR circulating nucleic acid (CNA) fragments from BSE and BSE-exposed cows shared an 80-mer base sequence homologous to the SINE Bov-tA found in the flanking regions of the bovine prion coding gene exons.

Experiments were performed as follows:

Experimental Protocol

Animals: Holstein cows primarily located in northwest Germany were used for the study. BSE-positive animals are defined as cattle in which a European Union-approved test for protease resistant prion protein ($PrP^{res}$) in the brain stem showed a positive result and was confirmed by immune histochemistry. Serum of BSE cows was drawn ante mortem from cows referred to the Institute of Veterinary Medicine as suspicious and confirmed as $PrP^{res}$-positive post mortem. Feeding cohorts (cohorts) are defined according to the official EU definition as being raised or born on the same farm within 12 months prior to or after the BSE index case. According to the official German BSE statistics (2001/2002/2003) ([Zahl der durchgeführten BSE-Tests im Berichtszeitraum] (2003)), it is calculated that such cows have an 107-fold increased risk of suffering from BSE as defined by $PrP^{res}$ accumulation in the brain stem at the time of BSE diagnosis of the index case (Table 1). Sera from cohorts were obtained at the day of culling, drawn and stored under the same standard conditions as BSE and control specimens. All cohorts that could be acquired during the study period were used if the group number exceeded n=7 for statistical reasons. Healthy control cattle are defined as randomly selected dairy cows from a farm where no BSE-confirmed animal has ever been detected, i.e., no animal slaughtered from the farm has shown positive results with an approved BSE post mortem test. The majority of normal control cattle sera was collected in a slaughterhouse at the time of slaughter. All cohort cattle and cattle acquired from the slaughterhouse used as normal controls were tested with an EU approved test for PrPres in the brain stem and found to be negative. Blood from these groups was drawn ante mortem. All cows tested were from farms in Northern Germany and did not differ in age or husbandry between the groups.

TABLE 1

Summation statistics from 2001 to 2003 of German BSE eradication program.

| | Number of Animals | | % $PrP^{res}$ |
|---|---|---|---|
| | $PrP^{res}$ Positive | $PrP^{res}$ Negative | Positive |
| Regular slaughterhouse samples | 103 | 7.7 × 10$^6$ | 0.0013 |
| Cohort cows | 8 | 5.58 × 10$^3$ | 0.14 |
| ODDS ratio | — | — | 107 (48.5-227)* |

*The difference in BSE incidence between the population of cows that has been regularly slaughtered and cohort cows is highly significant (p < 0.001; Chi2). Lower and upper limit of 95% confidence interval in parenthesis.

Serum collection: Special care was taken in collection, processing and storage of serum samples. Blood from the tail vein or artery was collected into 18 mL plastic tubes equipped with a coagulation accelerator and kept at room temperature for 30 min to ensure proper coagulation. Until further processing, the tubes were stored at 2-8° C. for not longer than 24 hours. Centrifugation was done at 2-8° C., 1000×g for 15 min. The serum supernatant was transferred into 1.5 mL microcentrifuge cups in 0.5 mL aliquots and frozen immediately at −20° C. or −80° C. until use Preparation of serum fractions: Frozen serum was thawed at 4° C. in an ice-water bath or refrigerator and 250 μL were transferred into a 1.5 mL microcentrifuge tube. The tube was centrifuged at 4,000×g for 25 min at 4° C. in a Model 5214 bench top centrifuge (Eppendorf, Hamburg, Germany) to remove cell debris. The supernatant was transferred into a fresh tube and subjected to 35 min centrifugation at 20,000×g. The supernatant was carefully removed and the pellet was used for further analyses.

Nucleic acid extraction: 20,000×g pellets were used with a standard silica based nucleic acid extraction (NucleoSpin Kit; Cat#: K3064, BD-Clontech, Heidelberg, Germany; field study: NucleoMag Kit, Macherey & Nagel, Düren, Germany) according to the manufacturer's instructions. The resulting nucleic acid solutions were either used immediately or frozen at −80° C. until further use.

Primer selection: BSE-enriched gene sequences were cloned and sequenced from sera collected from living animals eventually confirmed post mortem as BSE-positive. Two BSE cattle and four normal controls were used. Briefly, bovine blood was collected ante mortem via venipuncture from two BSE-positive cows (as confirmed at necropsy) and four healthy control cows. Nucleic acids (NA) were isolated from 250 μL of serum using solid phase (NucleoSpin Kit; Cat#: K3064, BD-Clontech, Heidelberg, Germany). A set of oligonucleotide primers with partially degenerate sequences was used for differential display. All partially degenerate primers contained a modified T7 signal sequence (5') followed by a unique stem sequence of 4 to 6 bp, followed by a stretch of 4N and one final unambiguous base. The stem sequences were selected from preceding subtraction experiments based on their preferential association to BSE cows over healthy controls (EMBL Acc. No. AJ620369-AJ620413). Partially degenerate primers were used in multiple combinations of 2 to 6 per PCR. 2 μL extracted NA was used as template in 20 μL PCR (Advantage-2 PCR Kit, BD-Clontech, Heidelberg, Germany), with 30 to 35 cycles at 48 to 55° C. annealing (60 sec), 68° C. extension (2 min), 94° C. denaturation (1 min). Samples from BSE confirmed cases and healthy control cows were loaded side-by-side on a PAGE gel and analyzed as described. Clearly differentially expressed bands, i.e., bands observed in all lanes from BSE-confirmed samples but not in lanes from healthy control samples, were cut out of gels, eluted and subjected to re-amplification with T7 primers. The products were first blunt-ended with T7 DNA polymerase and phosphorylated with PNK and ATP. This reaction mixture was used for blunt-end ligation into a SmaI-digested, dephosphorylated pGEM-4Z vector. Ligation was performed overnight at 4° C. using 1U T7 DNA ligase, 1 μg of the vector prepared as described and the PCR product prepared as described above. The product was transformed into chemically competent *E. coli* and plated on TAXI LB agar (tetracycline, ampicillin, X-Gal, IPTG). After overnight incubation at 37° C., positive (white) clones were picked and cultured in 1.5 mL LB-medium with ampicillin. Bacteria were harvested and plasmids were isolated according to standard protocols, and reconstituted in 50 μL TBE buffer. The plasmids were sequenced using either a LICOR model 4200 DNA sequencer with IRD700 labeled M13 forward and M13 reverse primers or with a model 3100 ABI capillary sequencer using unlabelled primers with big-dye-termination. From these sequences, candidate primer pairs were designed by standard techniques and used for further analyses so as to select the optimum combination that achieved separation of BSE from Normals. Primer selection can be done by manual inspection or several programs (e.g., Primer3: http://frodo.wi.mit.edu/cgi-bin/primer3/primer3_www.cgi), considering the basics of PCR primer design as published (see, e.g., Rychlik, et al., *Nucleic Acids Res.* 18:6409-6412, 1990; Rozen & Skaletsky, Primer3 on the WWW for general users and for biologist programmers. In: Krawetz S, Misener S (eds) *Bioinformatics Methods and Protocols: Methods in Molecular Biology* Humana Press, Totowa, N.J., pp 365-386, 2000). The respective annealing temperature for PCR is often estimated by the Wallace-Ikatura rule or the modification by Wu et al., whereas the best prediction of optimal annealing temperature can be achieved using thermodynamic nearest-neighbor calculations (see, e.g., von Ahsen et al. *Clin. Chem.* 47:1956-61, 2001).

The best separating primer combination, i.e., from the above analysis, was designated "CHX-1F" and "CHX-1R." CHX-1F is homologous to a cDNA bovine entry similar to calmodulin (Accession no. XM_592316), whereas CHX-1R is homologous to the monomer unit of Bov-tA (Accession no. X64124).

Sequencing: Primers CHX-1F and CHX-1R (Cat#: 42-4103 and 42-91102, Chronix Biomedical GmbH, Göttingen, Germany) were used on extracted NA in 20 μL PCR (Advantage-2 PCR Kit, BD-Clontech, Heidelberg, Germany), with 30 to 35 cycles at 48 to 55° C. annealing (60 sec), 68° C. extension (2 min), 94° C. denaturation (1 min). Samples from BSE confirmed cases and healthy control cows were loaded side-by-side on a PAGE gel and analyzed as described. Bands were cut out of gels, eluted and subjected to re-amplification. The products were cloned and sequenced.

Raw sequences were processed using Sequencher® (MAC OSX). Briefly, after trimming for the used cloning vector and ambiguities, an automatic contig assembly was performed using the default stringency parameters. From the resulting contigs, only those that included clones from at least two different samples were selected. Homologs were then defined as that portion of the contig sequence that was covered by more than 50% of the individual clones. The final homologous sequences were checked for the presence of the used primers. All homologs had one primer sequence; 18 homologs had both primer sequences present.

Blast analysis: Genetic analysis was applied to the sequences using the Advance Blast program (http://www.ncbi.nlm.nih.gov/BLAST/). The following parameters were set using the 'Megablast' sub-program: 'Low complexity' filter—off, 'Expect'—1000, 'Word size'—7. All hits were compared by order and length and the longest homologies of each region were used for comparisons. Analyses were done using the 'nr' database and 'est' database.

Nucleotide sequence accession numbers: The sequences of PCR products from BSE and BSE-exposed cows based on primers CHX 1F and CHX 1R were deposited with the EMBL database (Acc. No. AJ780924 to AJ780929).

Diagnostic PCR. Three μL of the extracted NA from serum fractions were used in a PCR in a total volume of 20 μL. For this analysis, the NU extract was not subjected to DNase treatment. Primers CHX-1F and CHX-CHT-1R (Cat#: 42-4103 and 42-91102, Chronix Biomedical GmbH, Göttingen, Germany), were used at 1 μM each using a proof reading polymerase system (Advantage-2 PCR Kit, BD-Clontech, Heidelberg, Germany). After 30 cycles of 95° C. for 30 sec, 55° C. for 45 sec, 68° C. for 1 min, a SybrGreenI (Cat#: S7563, Molecular Probes, Eugene, Oreg., USA) derived melting curve was recorded in a MX4000 PCR system (Cat#: 401260, Stratagene, La Jolla, Calif., USA). The area under the curve (AUC) of the derived melting function—d(F)/dT between 87° C. and 90° C. was used for analysis. This range was used as it was not prone to the influence of non-specific products, e.g., primer-dimers, which frequently may be present due to the use of SybrGreenI during PCR. Reactivity of each individual sample was calculated on the basis of an AUC above the detections limit, which is defined as mean +5 standard deviations above baseline of non-template or reference controls. All initially reactive samples were retested in duplicate. Samples sowing reactivity upon retesting were defined as repeatedly reactive.

Statistical analysis. The proportion of reactivity in the cohort groups and the healthy control groups was calculated. The statistical significance between the cohorts and healthy controls was estimated using the Chi-square test. For total group comparisons, a calculation with 9 degrees of freedom has been done, whereas for two group comparison the degrees of freedom was lowered to 1.

PAGE: Eight μL of the PCR mixture was mixed with loading buffer and applied to a precast 12-20% polyacrylamide gel in TBE buffer (45 mM Tris, 45 mM boric acid, 1 mM EDTA) (Novex 4-20% TBE Gel; Cat#: EC62255, Karlsruhe, Germany). Electrophoresis was run at ambient temperature, for 45 min at 180 V. The gels were stained for 20 min in a SybrGold (Cat#: S11494, Molecular Probes, USA) solution and were photographed under UV light.

Results

Enriching for disease-associated amplicons was accomplished by using degenerate primers in the amplification of BSE and healthy sera. The resulting amplicons were separated on PAGE gels and bands unique to BSE samples, i.e., bands that were observed in all lanes from BSE-confirmed samples but not in lanes from healthy control samples, were cut out, cloned and sequenced. From these sequences, unique candidate primers were selected for their ability to show significant separation of samples from BSE-confirmed animals over samples from healthy controls, e.g., using PCR or PAGE gels.

A primer derived from a 3' SINE region (CHX-1R) was evaluated by PCR and differential display for its utility in separation of signal from sera of healthy and diseased cattle. Samples from BSE confirmed cows, BSE-exposed at-risk cohorts, and healthy animals were used. One primer pair (CHX-1F/CHX-1R) showed no reactivity with a control group of healthy animals, but gave consistent amplification with BSE-exposed cattle. CHX-1F/CHX-1R was used to amplify CNA from two BSE-confirmed samples, $PrP^{res}$-negative cohort sera and healthy control cows. FIG. 1A shows a representative PAGE gel pattern of the PCR products using this primer pair in these groups. Similar multiple banding patterns can be observed for both BSE sera and all four cohort sera, whereas no reactivity is seen in normal control animals. FIG. 1B shows the result of melting curve analysis (Wittwer, et al., *Clin Chem* 49:853-60, 2003) of these samples. The melting patterns of both BSE and all four cohort sera show a similar wide-range reaction pattern, whereas a non-reactive pattern was observed in the healthy control samples.

To elucidate the nature of the resulting PCR product, amplicons from two BSE cases and srx BSE cohort animals were cloned and sequenced. The range of fragment sizes was from 105 to 304 bp with an average size of 210 bp. A stretch of an average of 80 bp was found in 150 out of 163 CAN-derived clones. This 80 bp stretch was identified as part of a short interspersed nucleotide element (SINE) referred to as Bov-tA. Three representative CAN fragments are shown in FIG. 2. CNA4 (AJ780927) was identified in both the BSE cases and cohort cows; CNA6 (AJ780928) and CNA1 (AJ780924) were CNA fragments from cohort sera with BSE cow 1 (CNA6) and BSE cow 2 (CNA1).

The depicted homologies downstream of the SINE are those database entries with the highest homology to the respective CNA sequences. The downstream sequences adjacent to the SINE fragment cannot be found in the genome contiguously; i.e., they are chimeric sequences consisting of truncated genomic DNA. Analysis of the clones shows that there were twenty one total homologs representing one hundred sixty three clones. Nineteen out of the twenty one homologs had a detectable Bov-tA SINE fragment. All nineteen homologs contained unique contiguous regions 3' to the Bov-tA SINE fragment. The nineteen unique regions represented short sequences ranging from 11mers to 83mers homologous with bovine genomic entries in the non-redundant BLAST database.

The data suggest that multiple nucleic acid sequences may be involved in defining the difference between normal and BSE-exposed cattle. The melting curve approach was selected because an entire PCR product profile can be generated. Using the CHX1F/1R primers, the melting curve protocol was further applied to a study of four confirmed BSE cases, eight unrelated $PrP^{res}$-negative cohorts (n=135) from BSE cases and 176 healthy control cows (Table 2). To avoid a regional bias, 148 samples from a slaughterhouse processing cattle from the same area where the BSE cases developed were selected randomly and included in the healthy control group together with 28 samples from a BSE non-exposed healthy control herd. The parameter used to calculate reactivity in this PCR differential display used AUCs. The AUCs were calculated according to the trapezoidal rule on the melting curves as exemplified in FIG. 1B. FIG. 3 shows that a range from 33% to 91% of cohorts demonstrated detectable CNA, an average of 63% for all cohorts tested, while only one of 176 healthy control samples (0.6%) showed a positive repeated reactivity. In addition, four of four sera from confirmed $PrP^{res}$ positive BSE cows showed positive results. These results are statistically significant ($p<0.001$); if calculated separately, every individual cohort group has a significantly ($p<0.001$) increased reactivity compared to the healthy controls. In a field study, an additional set of 669 samples from a slaughterhouse were tested. These additional samples originated from 257 different farms and did not differ significantly from the cohort groups in age (60.7; 30-90 vs. 61.3; 37-91; age in months, average with $10^{th}$ to $90^{th}$ percentile) or regional origin (Northern Germany). Samples from known cohorts served as positive controls and yielded 58% repeated reactivity, which was in the middle of the assigned value (50% to 69%). Only 4 samples from the field study were found to be repeatedly reactive (0.59%), which confirms the results with the previous group of 176 normal control cattle.

TABLE 2

Study populations

| Designation | Sample Size | Age of BSE Indicator Case (mo) |
|---|---|---|
| BSE cohort 15/03 | 14 | 64 |
| BSE cohort 19/03 | 35 | 55 |
| BSE cohort 02/02 | 18 | 60 |
| BSE cohort 12/03 | 16 | 50 |
| BSE cohort 14/02 | 11 | 71 |
| BSE cohort 42/02 | 17 | 83 |
| BSE cohort 45/02 | 11 | 93 |
| BSE cohort 44/03 | 13 | 65 |
| Healthy control herd | 28 | (27-79)[a] |
| Random healthy controls[b] | 148 | (24-90)[a] |

[a]Age range (months) of healthy control cows
[b]Cows randomly selected from slaughterhouse Discussion The presence of CNA in the sera of cattle was reported previously (e.g., Brenig, et al., *Berl Münch Tierärztl Wochenschr* 115:122-4, 2002). The present study was conducted to determine whether BSE exposure correlates with the appearance CNA, e.g., serum SINE-associated CNA. BSE was evaluated for several reasons: 1) BSE is a naturally-occurring veterinary chronic illness, 2) clinical samples with sufficient volumes of sera and associated records were available (although the number of BSE-confirmed cases available was limited in this study), and 3) there is an associated at-risk population of animals.

BSE-confirmed and BSE at-risk animals from exposed cohorts of $PrP^{res}$-confirmed BSE index cases were defined as BSE-exposed cases. The rationale for studying at-risk cohorts is clear from Table 1. According to the data provided by the German Ministry of Consumer Safety, Nutrition and Agriculture, the likelihood of detecting a PrP$^{res}$-positive animal amongst cohorts is more than 100-fold greater than in healthy, non-cohort cattle. Such BSE cohort cattle are in fact challenged with the same contaminated chow as the BSE index case. Approximately 1000 cattle were used in this study to confirm the feasibility of a PCR test to detect SINE-associated CNA as an ante mortem surrogate marker for BSE exposure.

Three major findings arose from the study of SINE associated CNAs in BSE. First, the 3' region of Bov-tA fragments was detected in the PCR products derived from serum of confirmed BSE cases or BSE-exposed cohorts. The genomes of ruminants contain three related SINE elements: Bov-tA, Bov-A2, and Bov-B. The Bov-tA element, which is present in about 285,000 copies comprising approximately 1.6% of the bovine genome, is a tRNA$^{Gly}$ pseudogene (see, e.g., Lenstra, et al., *Anim Genet* 24:33-9, 1993). It is frequently present within the 3'-UTR of genes. Compared to the other bovine SINEs, the Bov-tA elements are relatively heterogeneous, harboring a 73 bp stretch of the tRNA$^{Gly}$ gene (see, e.g., Sakamoto & Okada, *J Mol Evol* 22:134-40, 1985), 115 bp of a central monomeric region and a short 3'-repeat region of 2-6 bp sequence elements. The variability within the DNA sequences of the Bov-tA elements suggests that these elements are evolutionarily older fragments. The 3' SINE fragment derived from BSE associated CNAs was an average of 80 bp consensus sequence revealing an expected range of homology (81% to 94%) with heterogeneous Bov-tA repetitive sequences.

The significance of detecting SINE fragments in CNA fractions is that the expression of SINE elements is associated with cell stress. Studying human SINEs (Alus), Liu et al. (*Nucleic Acids Res* 23:1758-65, 1995) reported that cells stressed by exposure to cycloheximide or puromycin "rapidly and transiently increased the abundance of Alu RNA." Kalkkila et al. (Eur J Neurosci 19:1199-206, 2004) reported in a Mongolian gerbil model that SINE B1 and B2 transcripts could be detected in the CA1 region of the hippocampus after ischemia induction. The authors concluded that SINE elements are "stress-inducible factors in the central nervous system." Our finding of SINE associated CNA common to both BSE and BSE-exposed cohorts suggests that there may be an underlying cell stress condition associated with BSE. The concept of an underlying condition fits well with the observation from an experimental model that cattle exposed to infective material at doses equivalent to contaminated cattle chow develop the disease at an incidence of less than 10% at 6 years post-exposure (Lasmezas, et al., *Lancet* 365:781-3, 2005). The failure to reach higher infection frequency with low dose exposure implies underlying complex dynamics of BSE clinical development and therefore may reflect the contribution of cell stress associated etiopathological mechanisms for the manifestation of BSE.

The second major finding from this study was that the 3' SINE fragment-associated PCR CNA products were contiguous with unique sequences of variant lengths. It would appear that the unique sequence may in fact be chimeric sequences from germ-line DNA as determined from NCBI BLAST analysis. 150 out of 163 clones (92%) had a 3' SINE fragment (sizes ranged from 52 to 87 bp) with the homology to Bov-tA. These 150 clones corresponded to 19 homologs. The 19 Bov-tA-containing homologs had unique downstream sequences that varied in length from 19 bp to 214 bp. NCBI BLAST analysis indicated that these downstream sequences are composed of 11 mer to 83 mer sequences present in the bovine genome. The downstream sequences are linked at the 5' end of the monomer unit of Bov-tA, which is equivalent to the proposed harbor position of ALU (see, e.g., Babcock et al., *Genome Res* 13:2519-32, 2003).

SINE and Alu sequences are known to be strongly involved in recombinatorial events (see, e.g., Schmid, *Nucleic Acids Res* 26:4541-50, 1998; Urnovitz, et al., *Clin Diagn Lab Immunol* 6:330-5, 1999). The unique sequences found downstream from the SINE sequence appear to be rearrangements of bovine germ-line sequences.

The third major finding from this study is that repeatedly-reactive CNA patterns are found in BSE at-risk, PrP$^{res}$-negative cows. As mentioned above, cohort animals, which are exposed to the infectious agent together with the BSE index case during the first years of their lives, are 100 times more likely to become PrP$^{res}$-positive than non-cohort animals (Table 1). Such BSE-exposed cohorts showed a range from 33% to 91% repeatedly reactive individuals per cohort in 8 out of 8 PrP$^{res}$-negative cohorts. The resulting PCR products generated by repeatedly reactive PrP$^{res}$-negative cohort animals were similar to the PCR products from four cases of confirmed BSE. In the specificity study, only 5 samples out of 845 combined healthy controls (0.59%) showed repeated reactivity. These data suggest that there is a low incidence of CHX-1R specific SINE associated CNAs in the healthy control population.

The presence of a 3' SINE element-associated CNA supports the notion that SINE detection might be a useful early stage disease marker of a cell stress-associated clinical disease. The results of this study using primers CHX-1F and CHX-1R show that the general bovine population expresses a low incidence of specific detectable SINE associated CNAs, while BSE-exposed cohorts are 63% repeatedly reactive. The CNAs are found in fractions that are enriched for microparticles (exosomes and plasma membrane microvesicles). Fevrier and Raposo have proposed that exosomes/microvesicles are involved in extracellular messaging. Further, they note that detection of scrapie prions in exosomes has been reported (Fevrier, et al., *Proc Natl Acad Sci USA* 101:9683-8, 2004). Although nucleic acids have been reported to be associated with misfolded prions (Manuelidis, *Viral Immunol* 16:123-39, 2003) it is not clear if the unique CNAs detected in this study might be involved in such association.

The results of this study identified genetic sequences associated with BSE and BSE exposure and support the laboratory diagnostic use of circulating nucleic acids for detecting BSE-exposed animals. Future studies should be able to determine whether the unique fragments associated with SINE CNA can reveal the cell or cells of origin and consequently define the associated clinical diseases in terms of diagnostic criteria.

Example 2

Use of Alternative Primer Sets to Identify Animals at Risk

Any number of primer pairs can be used in the detection methods of the invention. This example provides alternative exemplary primer pairs.

Primer #55 corresponds to 18 nucleotides within a consensus SINE sequence (M26330 Bovine short interspersed repetitive sequences found in genomic DNA) that repeats itself multiple times in bovine genome in direct and reverse orientation, including twelve repeats within PrP gene (AJ298878 Bos taurus PrP gene for prion protein). Primers #60-63 correspond to PrP sequences located 150-1000 bp upstream (60F, 61F, 62F, and 63F) or downstream (60R, 61R, 62R, or 63R) from the consensus primer sequence #55.

In addition to these primers, a control set of primers (PG01, PG02) directed against the non-translated region of enteroviruses was used.

```
Primer 5'-cttgcctggagaatccca-3'      (SEQ ID NO:3)
55F

Primer 5'-gggattctccaggcaaga-3'      (SEQ ID NO:4)
55R

Primer 5'-gcatgttcctttcagaa-3'       (SEQ ID NO:5)
60F

Primer 5'-gttgcttcagtcgtgtcc-3'      (SEQ ID NO:6)
60R

Primer 5'-ctgtgtcctaggaatgcat-3'     (SEQ ID NO:7)
61R

Primer 5'-gcatcaaagcactgtacgtt-3'    (SEQ ID NO:8)
62F

Primer 5'-gccttctagagtcaaccaaga-3'   (SEQ ID NO:9)
62R

Primer 5'-cgtgcaatgcaggagaccagg-3'   (SEQ ID NO:10)
63F

Primer 5'-gctgtgacatttcttgatag-3'    (SEQ ID NO:11)
63R

Primer pair:PG01-5 and PG02-5
PG01-  5'-aagcacttctgtttc-3'         (SEQ ID NO:12)
5:

PG02-  5'-cattcagggccggagga-3'       (SEQ ID NO:13)
5:
```

Figure 4:
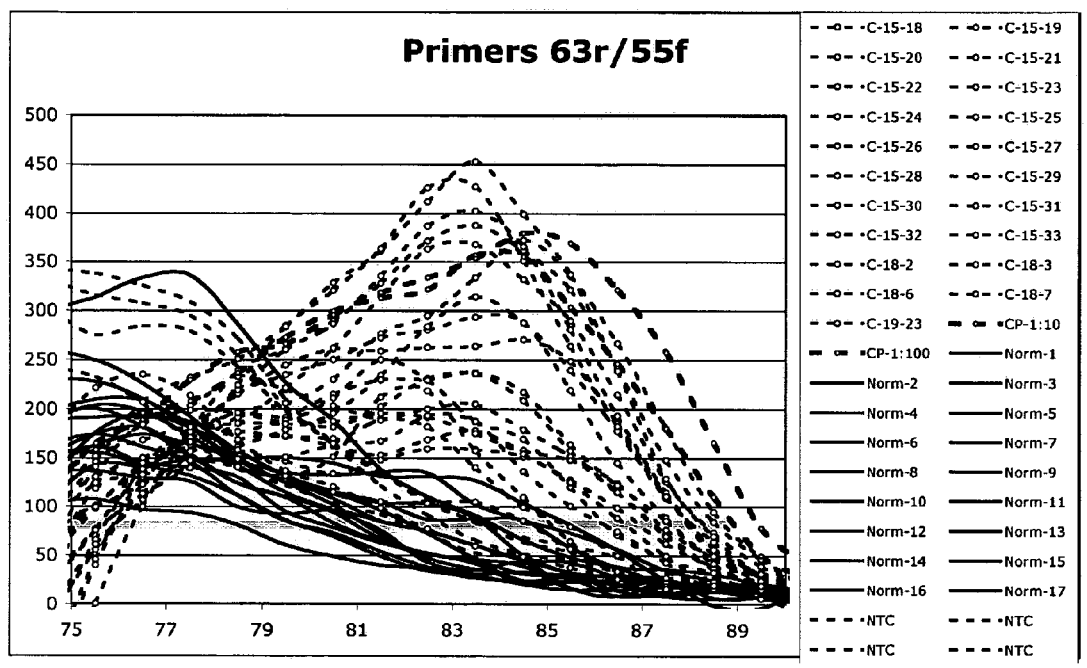
FIG. 4 provides an exemplary melting curve analysis of cohort vs. normal (SH=slaughterhouse) of nucleic acids isolated from serum samples. The PCR was performed using primers 63R/55F. (cohort samples, open circles; normal samples, solid lines; non-template controls, dotted lines)
Figure 5:
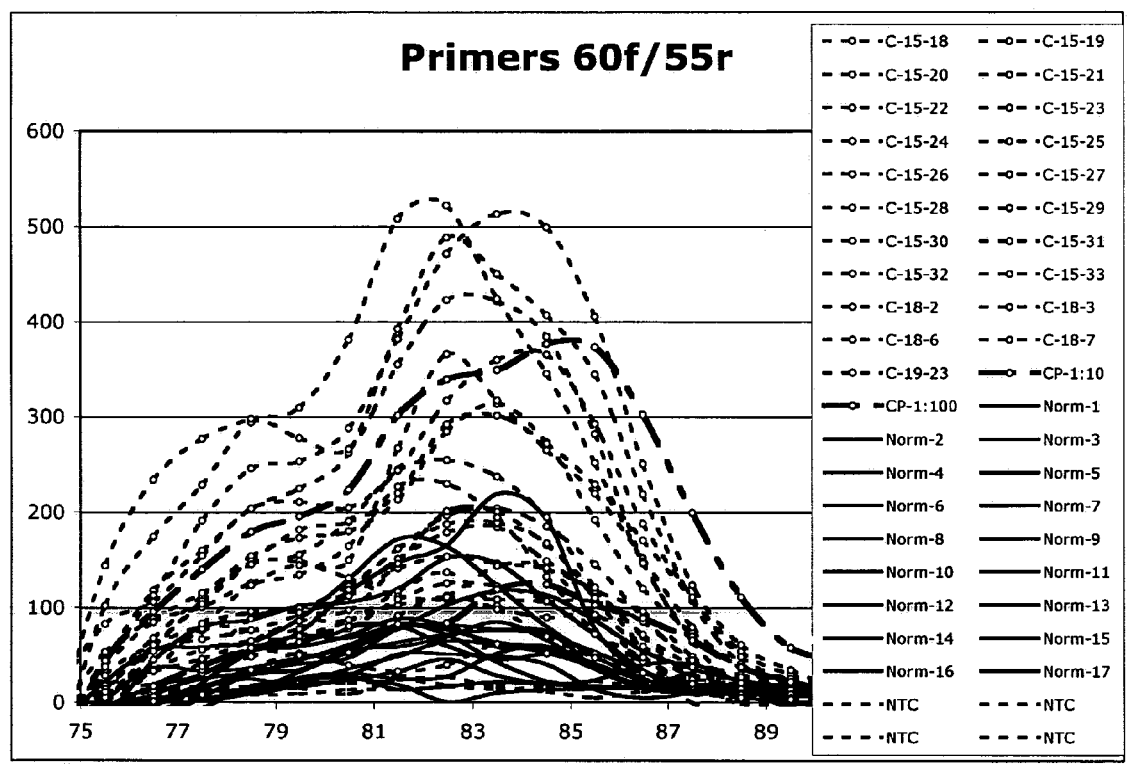
FIG. 5 provides an exemplary melting curve analysis of cohort vs. normal (SH=slaughterhouse) of nucleic acids isolated from serum samples. The PCR was performed using primers 60F/55R. (cohort samples, open circles; normal samples, solid lines; non-template controls, dotted lines)
Figure 6:
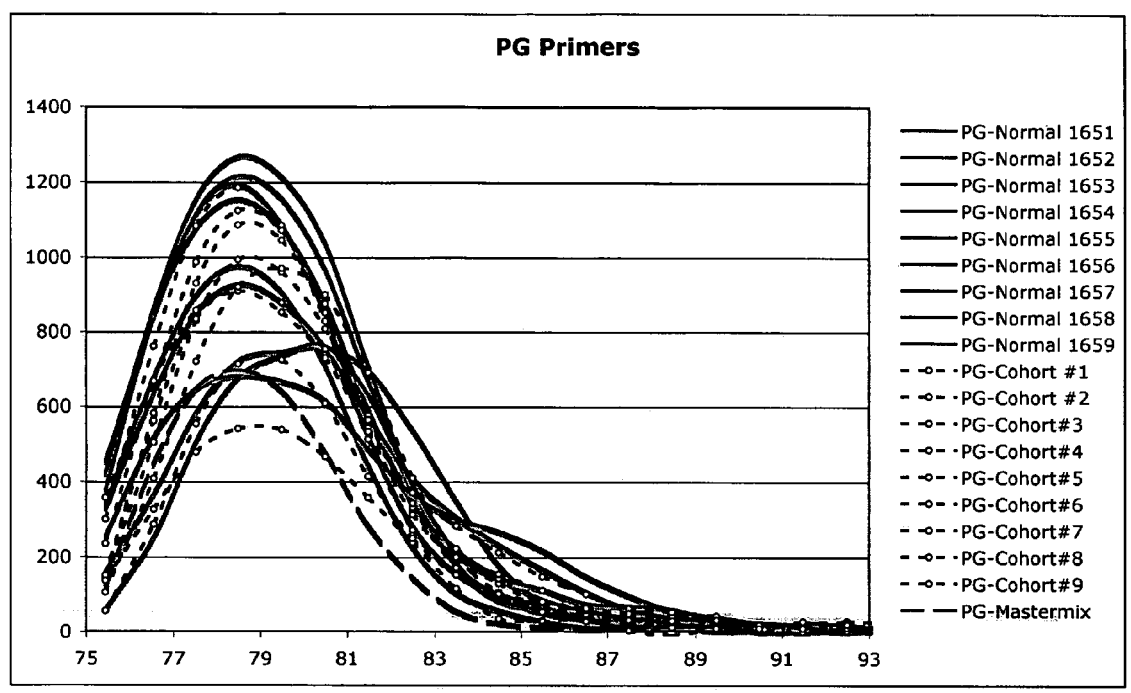
FIG. 6 provides an exemplary melting curve analysis of cohort vs. normal (SH=slaughterhouse) of nucleic acids isolated from serum samples. The PCR was performed using primers PGO1/PGO2. (cohort samples, open circles; normal samples, solid lines)

Melting curve analyses were performed on PCR analyses conducted with cohort and healthy control animals for PCR conditions were those described in Example 1. Melting curve analysis performed with primers 63R and 55F resulted in melting patterns of cohort sera that showed a range of similar reaction pattern, whereas a consistent non-reactive pattern was observed in the healthy control samples (FIG. 4). Melting curve analysis performed with primers 60F and 55R also showed profiles in which the cohort samples were consistently reactive, but the normal controls were not (FIG. 5). Melting curve analysis performed with the PGO1 and PGO2 did not show any notable differences between cohort and normal samples (FIG. 6), nor did melt curve analysis performed with primer pairs 62R/55R, 60F/55F, and 2F/55R.

Example 3

Use of Serum or Plasma as Acellular Sample

Figure 7:
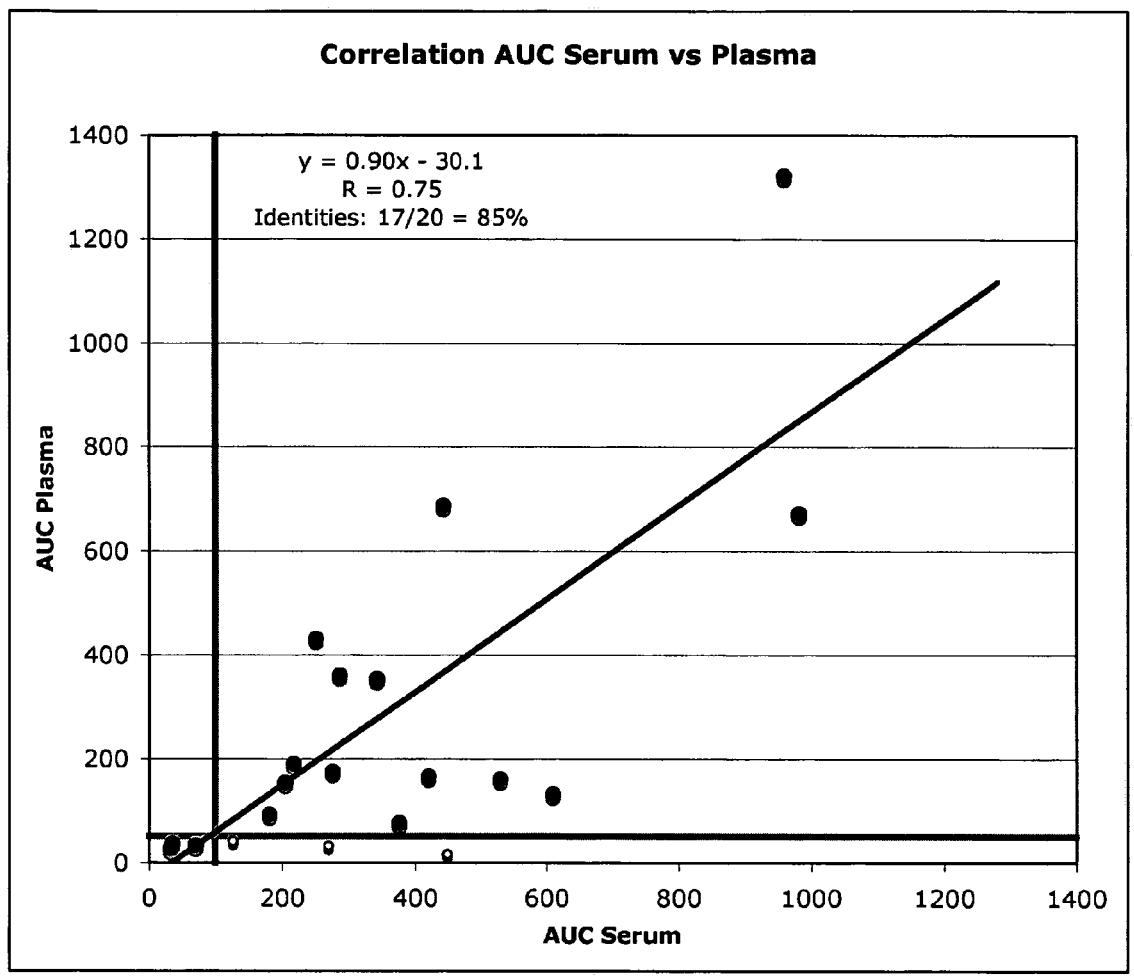
FIG. 7 shows exemplary data comparing analyses performed with serum vs. those performed with plasma.

This example shows that plasma samples can also be used. The analysis was performed using the primers CHX-1F and CHX-1R and PCR conditions shown in Example 1. The results using plasma samples were correlated to results obtained analyzing serum samples from the same animals. The results are shown in FIG. 7.

The above examples are provided to illustrate the invention but not to limit its scope. Other variants of the invention will be readily apparent to one of ordinary skill in the art and are encompassed by the appended claims.

All publications, patents, accession numbers, and patent applications cited herein are hereby incorporated by reference for all purposes.

What is claimed is:

1. A method of detecting an animal at increased risk for bovine spongiform encephalopathy (BSE), the method comprising:

incubating nucleic acids extracted from an acellular sample obtained from the animal with amplification primers in a test amplification reaction; wherein the amplification primers comprise: (i) at least 10 contiguous nucleotides of CHX-1F (SEQ ID NO:1) and CHX-1R (SEQ ID NO:2) or (ii) CHX-1F (SEQ ID NO:1) and CHX-1R (SEQ ID NO:2) or (iii) 63R (SEQ ID NO: 11) and 55F (SEQ ID NO: 3); or 60F (SEQ ID NO: 5) and 55R (SEQ ID NO: 4);

detecting reactivity of the amplification reaction that is over 5 standard deviations from a reference amplification reaction, wherein reactivity of over 5 is indicative of an increased risk for BSE, wherein reactivity of the amplification reaction is determined using a melting curve.

2. The method of claim 1, wherein the acellular fluid sample is serum.

3. The method of claim 1, wherein the acellular fluid sample is plasma.

4. The method of claim 1, wherein one of the primers comprises sequences that hybridize to repetitive sequences in the animal genome.

5. The method of claim 4, wherein the repetitive sequences are SINE sequences.

6. The method of claim 1, wherein the nucleic acid sample comprises DNA.

7. The method of claim 1, wherein the amplification reactions comprise a compound that specifically binds to double-stranded DNA.

8. The method of claim 7, wherein the compound is a fluorescent dye.

9. The method of claim 1, wherein the amplification primers comprise CHX-1F (SEQ ID NO:1) and CHX-1R (SEQ ID NO:2).

10. The method of claim 1, wherein the amplification primers comprise 63R and 55F; or 60F and 55R.

* * * * *